United States Patent [19]

Grohe

[11] Patent Number: 4,699,992
[45] Date of Patent: Oct. 13, 1987

[54] 3-AMINO-2-BENZOYLACRYLIC ACID DERIVATIVES

[75] Inventor: Klaus Grohe, Odenthal, Fed. Rep. of Germany

[73] Assignee: Bayer Aktiengesellschaft, Leverkusen, Fed. Rep. of Germany

[21] Appl. No.: 775,202

[22] Filed: Sep. 12, 1985

[30] Foreign Application Priority Data

Sep. 29, 1984 [DE] Fed. Rep. of Germany ....... 3435930
Jan. 30, 1985 [DE] Fed. Rep. of Germany ....... 3502935

[51] Int. Cl.$^4$ ................. C07C 121/78; C07C 69/533
[52] U.S. Cl. .................................. 558/405; 560/21; 560/22; 560/38; 564/163; 564/166; 564/168; 544/363
[58] Field of Search ................. 544/363; 560/38, 21, 560/22; 558/405; 564/163, 166, 168

[56] References Cited

U.S. PATENT DOCUMENTS 4,439,620  3/1984  Klauke et al. ................. 544/363 X

FOREIGN PATENT DOCUMENTS 0004279  12/1982  European Pat. Off. .

*Primary Examiner*—Dolph H. Torrence
*Attorney, Agent, or Firm*—Sprung Horn Kramer & Woods

[57] ABSTRACT

Novel 3-amino-2-benzoyl-acrylic acid derivatives of the formula

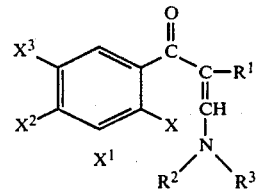

in which $R^1$ represents the nitrile group, an ester group —COOR$^4$ or carboxamide group

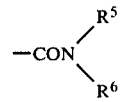

$R^4$ denoting $C_1$–$C_6$-alkyl, and
$R^5$ and $R^6$ representing hydrogen or $C_1$–$C_3$-alkyl or phenyl,
$R^2$ and $R^3$, which can be identical or different, represent a $C_1$–$C_6$-alkyl radical and, furthermore, can form, together with the nitrogen atom to which they are bonded, a 5- or 6-membered heterocyclic ring which can additionally contain as ring member the atoms or groups —O—, —S—, —SO— or —SO$_2$—,
X represents halogen,
$X^1$ denotes hydrogen, methyl, nitro or halogen,
$X^2$ denotes halogen or methyl, and
$X^3$ denotes hydrogen or halogen,
are prepared by reacting

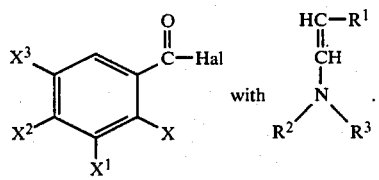

The products can be converted into known antibacterials.

6 Claims, No Drawings

3-AMINO-2-BENZOYLACRYLIC ACID DERIVATIVES

The present invention relates to 3-amino-2-benzoylacrylic acid derivatives, which are valuable intermediates for the synthesis of highly active antibacterial medicaments, and to a process for their preparation.

It has been found that 3-amino-2-benzoylacrylic acid derivatives of the formula I

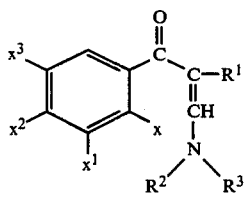

in which
R$^1$ represents the nitrile group, an ester group —COOR$^4$ or carboxamide group

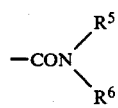

R$^4$ denoting C$_1$–C$_6$-alkyl, and
R$^5$ and R$^6$ representing hydrogen or C$_1$–C$_3$-alkyl or phenyl,
R$^2$ and R$^3$, which can be identical or different, represent a C$_1$–C$_6$-alkyl radical and, furthermore, can form, together with the nitrogen atom to which they are bonded, a 5- or 6-membered heterocyclic ring which can additionally contain as ring member the atoms or groups —O—, —S—, —SO— or —SO$_2$—,
X represents halogen, preferably chlorine or fluorine,
X$^1$ denotes hydrogen, methyl, nitro or halogen, preferably fluorine,
X$^2$ can be halogen, preferably chlorine or fluorine, or methyl, and
X$^3$ represents hydrogen or halogen, preferably fluorine, are obtained when benzoyl halides of the formula II, in which
Hal preferably denotes chlorine or bromine and X, X$^1$, X$^2$ and X$^3$ have the abovementioned meaning, are reacted with 3-aminoacrylic acid derivatives of the formula III
in which
R$^1$, R$^2$ and R$^3$ have the abovementioned meaning, where appropriate in the presence of a base:

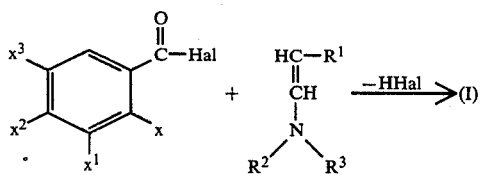

The 3-amino-2-benzoyl-acrylic acid derivatives I according to the invention can be converted with cyclopropylamine IV into the 3-cyclopropylamino-2-benzoylacrylic acid derivatives V, some of which are known and have already been synthesised by other routes:

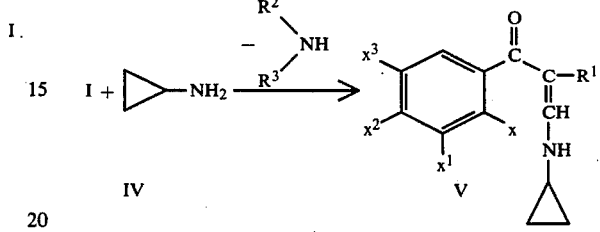

It has already been disclosed that monoalkylaminoacrylic acid derivatives III (R$^1$=COOR$^4$, R$^2$=H) are acylated with benzoyl halides II (European Patent No. 0,004,279), during which partial N-acylation occurs. In contrast, the process according to the invention has the advantage that only C-acylation of the enamine system takes place, which leads to a considerable increase in the yield.

When 2,4-dichloro-5-fluorobenzoyl chloride (1) and methyl 3-dimethylaminoacrylate (2) are used as the starting materials, then the course of the reaction according to the invention can be represented by the equation below:

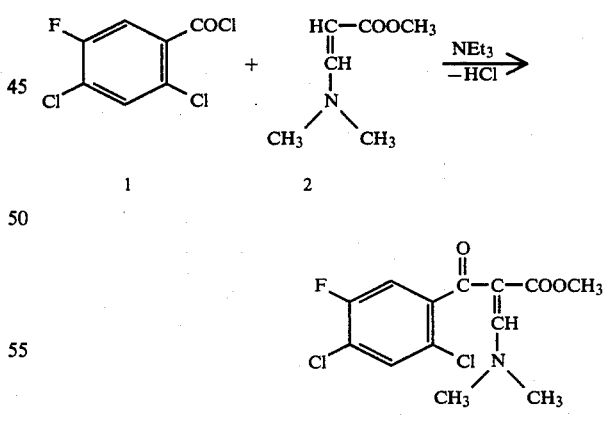

In the subseqeunt reaction of (3) with cyclopropylamine, the 3-cyclopropylaminoacrylic ester (4) is produced, and this can then be converted into the wide-spectrum antibacterial chemotherapeutic agent ciprofloxacin (see DE-OS (German Published Specification) 3,142,854):

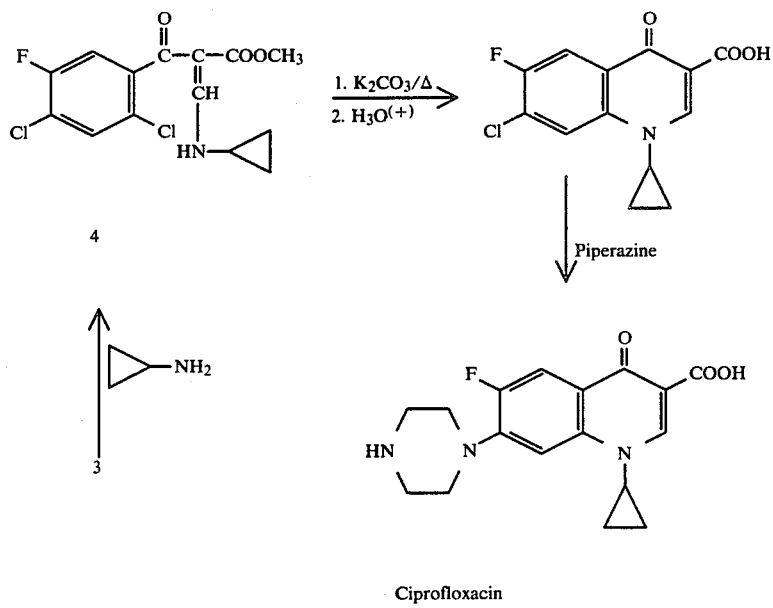

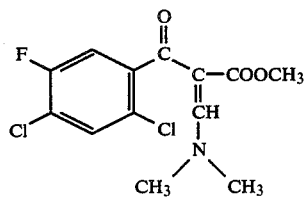

Ciprofloxacin

The fluorine- and chlorine-containing benzoyl halides II or the corresponding carboxylic acids, both of which can be used according to the invention, are known, for example from DE-OS (German Published Specification) No. 3,142,856.

The following may be mentioned as examples: 2,4-dichloro-5-fluorobenzoyl chloride, 2,4,5-trifluorobenzoyl chloride, 2,3,4,5-tetrafluorobenzoyl chloride, 2,4,5-trichlorobenzoyl chloride, 2,3,4,5-tetrachlorobenzoyl chloride and 2,4,5-trifluoro-3-chlorobenzoyl chloride.

The 3-aminoacrylic acid derivatives III are likewise known.

The following may be mentioned as examples: methyl 3-dimethylaminoacrylate, ethyl 3-dimethylaminoacrylate, 3-dimethylaminoacrylonitrile, 3-dimethylaminoacrylamide, the methylamide of 3-dimethylaminoacrylic acid, the dimethylamide of 3-dimethylaminoacrylic acid, and the anilide of 3-dimethylaminoacrylic acid.

The reaction of the halogenated benzoyl halides II with the 3-aminoacrylic acid derivatives III is preferably carried out in an inert diluent. Methylene chloride, chloroform, toluene, tetrahydrofuran and dioxane are suitable.

The reaction is carried out at temperatures between 10° and 200° C., preferably between 20° and 110° C. It is preferably carried out under atmospheric pressure.

The reactants II and III are preferably employed in the 1:1 stoichiometric ratio.

The acid acceptors which are preferably used are pyridine, triethylamine, N-methylpiperidine and sodium hydride.

The reaction of the 3-aminobenzoylacrylic acid derivatives I with cyclopropylamine IV to give V is preferably carried out in a diluent such as, for example, cyclohexane, toluene, dioxane, carbon tetrachloride or chlorobenzene, at temperatures from 10° to 200° C., preferably 20° to 120° C.

The compounds according to the invention are valuable intermediates for the preparation of highly active antibacterial medicaments which are described in, for example, DE-OS (German Published Specifications) Nos. 3,033,157 and 3,142,854.

EXAMPLE 1

Methyl 3-dimethylamino-2-(2,4-dichloro-5-fluorobenzoyl)acrylate

First a solution of 12.9 g of methyl 3-dimethylaminoacrylate in 25 ml of dioxane is added dropwise, and then 10.5 g of triethylamine are added to a solution of 22.75 g of 2,4-dichloro-5-fluorobenzoyl chloride in 80 ml of anhydrous dioxane, while cooling in ice and stirring. The mixture is stirred at room temperature for 3 hours, heated at 50°–60° C. for 1 hour, and the solvent is removed by distillation in vacuo and the residue is taken up in methylene chloride/$H_2O$. The phases are separated, and the aqueous solution is again extracted with methylene chloride. The combined organic phases are washed with water, dried with sodium sulphate, and the methylene chloride is removed in vacuo. The crystalline residue is recrystallized from methanol/water. 28.5 g of methyl 3-dimethylamino-2-(2,4-dichloro-5-fluorobenzoyl)acrylate of melting point 107°–109° C. are obtained.

EXAMPLE 2

Ethyl 3-dimethylamino-2-(2,4-dichloro-5-fluorobenzoyl)acrylate

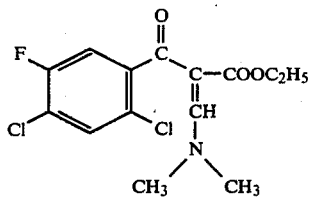

14.3 g of ethyl 3-dimethylaminoacrylate and 10.5 g of triethylamine are added dropwise to a solution of 22.75 g of 2,4-dichloro-5-fluorobenzoyl chloride in 100 ml of anhydrous dioxane at 10° to 20° C., with stirring. The mixture is stirred at room temperature for 3 hours, heated at 40°–50° C. for 1 hour, and the solvent is removed by distillation in vacuo and the residue is taken up in methylene chloride/H$_2$O. The phases are separated, and the aqueous solution is again extracted with methylene chloride. The CH$_2$Cl$_2$ solution is washed with water, dried with sodium sulphate, and the solvent is removed in vacuo. The crystalline residue is recrystallized from cyclohexane/light petroleum. 27.8 g of ethyl 3-dimethylamino-2-(2,4-dichloro-5-fluorobenzoyl)acrylate of melting point 94°–95° C. are obtained.

The reaction, which is described below, of this compound with cyclopropylamine leads to ethyl 3-cyclopropylamino-2-(2,4-dichloro-5-fluorobenzoyl)acrylate:

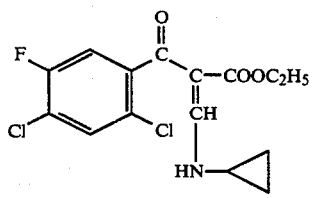

33.4 g of ethyl 3-dimethylamino-2-(2,4-dichloro-5-fluorobenzoyl)acrylate are heated to boiling under reflux with 7 g of cyclopropylamine and 120 ml of toluene for 1 hour. The gas evolution, the onset of which is initially violent, is then finished. The toluene is removed by distillation in vacuo, and the solid residue is recrystallized from light petroleum. 32.5 g of ethyl 3-cyclopropylamino-2-(2,4-dichloro-5-fluorobenzoyl)acrylate of melting point 89°–91° C. are obtained.

EXAMPLE 3

3-Dimethylamino-2-(2,4-dichloro-5-fluorobenzoyl)acrylonitrile

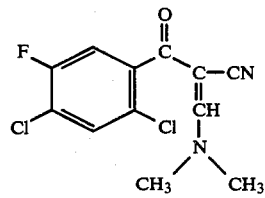

9.6 g of 3-dimethylaminoacrylonitrile and 10.5 g of triethylamine are added dropwise to a solution of 22.75 g of 2,4-dichloro-5-fluorobenzoyl chloride in 100 ml of anhydrous dioxane, while cooling in ice and stirring. The mixture is stirred at room temperature for 1 hour and then heated to boiling under reflux for 4 hours. The solvent is removed by distillation in vacuo, and the residue is taken up in methylene chloride/water. The methylene chloride phase is washed with water, dried with sodium sulphate, and evaporated in vacuo. The crystalline residue is recrystallized from ethanol. 22.2 g of 3-dimethylamino-2-(2,4-dichloro-5-fluorobenzoyl)acrylonitrile of melting point 138°–139° C. are obtained.

The reaction, which is described below, of this compound with cyclopropylamine leads to 3-cyclopropylamino-2-(2,4-dichloro-5-fluorobenzoyl)acrylonitrile:

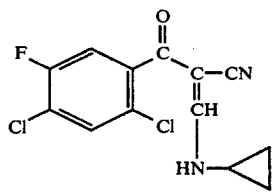

14.35 g of 3-dimethylamino-2-(2,4-dichloro-5-fluorobenzoyl)acrylonitrile are refluxed with 3.2 g of cyclopropylamine and 60 ml of toluene. When the evolution of gas is finished after about 30 minutes, the toluene is removed by distillation in vacuo, and the residue is recrystallized from ethanol/light petroleum. 13.8 g of 3-cyclopropylamino-2-(2,4-dichloro-5-fluorobenzoyl)acrylonitrile of melting point 94°–95° C. are obtained.

EXAMPLE 4

Dimethylamide of 3-dimethylamino-2-(2,4-dichloro-5-fluorobenzoyl)acrylic acid

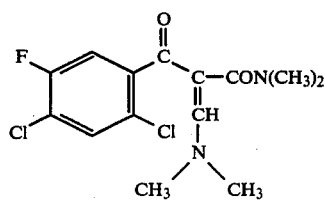

First 14.3 g of the dimethylamide of 3-dimethylaminoacrylic acid are added in portions, and then 10.5 g of triethylamine are added dropwise to a solution of 22.75 g of 2,4-dichloro-5-fluorobenzoyl chloride in 100 ml of anhydrous dioxane, while cooling in ice and stirring. The mixture is stirred at room temperature for 3 hours, and then heated at 50°–60° C. for a further 3 hours. The solvent is removed in vacuo, and the residue is partitioned between methylene chloride and water. The methylene chloride solution is washed with water, dried with sodium sulphate, and the solvent is removed in vacuo. The crystalline residue is recrystallized from ethanol/water. 21.5 g of the dimethylamide of 3-dimethylamino-2-(2,4-dichloro-5-fluorobenzoyl)acrylic acid of melting point 124°–126° C. are obtained.

EXAMPLE 5

Methyl 3-(1-pyrrolidinyl)-2-(2,4-dichloro-5-fluorobenzoyl)acrylate

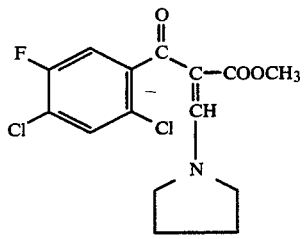

First a solution of 15.5 g of methyl 3-(1-pyrrolidinyl)acrylate in 25 ml of dioxane is added dropwise, and then 10.5 g of triethylamine are added to a solution of 22.75 g of 2,4-dichloro-5-fluorobenzoyl chloride in 80 ml of anhydrous dioxane, while cooling in ice and stirring. The mixture is stirred at room temperature for 1 hour, heated to boiling under reflux for 30 minutes, and the solvent is removed by distillation in vacuo, and the residue is taken up in methylene chloride/H$_2$O. The phases are separated and the aqueous solution is again extracted with methylene chloride. The combined organic phases are washed with water, dried with sodium sulphate, and the methylene chloride is removed in vacuo. The crystalline residue is recrystallized from cyclohexane. 19.6 g of methyl 3-(1-pyrrolidinyl)-2-(2,4-dichloro-5-fluorobenzoyl)acrylate of melting point 74°–76° C. are obtained.

The reaction, which is described below, of this compound with cyclopropylamine leads to methyl 3-cyclopropylamino-2-(2,4-dichloro-5-fluorobenzoyl)acrylate

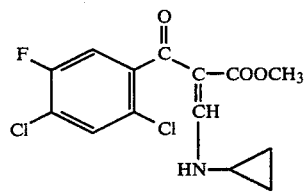

3.5 g of methyl 3-(1-pyrrolidinyl)-2-(2,4-dichloro-5-fluorobenzoyl)acrylate are heated to boiling under reflux with 0.8 g of cyclopropylamine and 50 ml of toluene for one hour. The toluene is removed by distillation in vacuo, and the residue is recrystallized from acetonitrile. 2.5 g of methyl 3-cyclopropylamino-2-(2,4-dichloro-5-fluorobenzoyl)acrylate of melting point 150°–151° C. are obtained.

EXAMPLE 6

Ethyl 3-diethylamino-2-(2,4-dichloro-5-fluorobenzoyl)acrylate

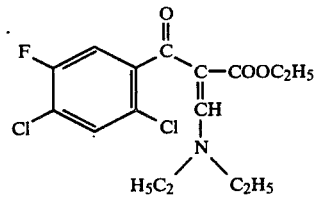

First 17.1 g of ethyl 3-diethylaminoacrylate are added dropwise and then 10.5 g of triethylamine are added to a solution of 22.75 g of 2,4-dichloro-5-fluorobenzoyl chloride in 80 ml of anhydrous dioxane, while cooling in ice and stirring. The mixture is stirred at room temperature for one hour, heated to boiling under reflux for 45 minutes, and the solvent is removed by distillation in vacuo, and the oily residue is taken up in methylene chloride/water. The phases are separated, and the aqueous solution is again extracted with methylene chloride. The combined organic phases are washed with water, dried with sodium sulphate, and the methylene chloride is removed in vacuo. 29 g of ethyl 3-diethylamino-2-(2,4-dichloro-5-fluorobenzoyl)acrylate are obtained as a brown oil.

The reaction, which is described below, of this compound with cyclopropylamine leads to ethyl 3-cyclopropylamino-2-(2,4-dichloro-5-fluorobenzoyl)acrylate:

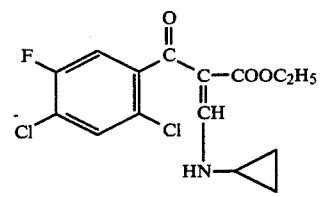

17.5 g of ethyl 3-diethylamino-2-(2,4-dichloro-5-fluorobenzoyl)acrylate are heated to boiling under reflux with 2.9 g of cyclopropylamine and 50 ml of toluene for 30 minutes. The toluene is removed by distillation in vacuo, and the residue, which solidifies to crystals, is recrystallized from cyclohexane/light petroleum. 12.9 g of ethyl 3-cyclopropylamino-2-(2,4-dichloro-5-fluorobenzoyl)acrylate of melting point 89°–90° C. are obtained.

EXAMPLE 7

3-Dimethylamino-2-(2,3,4,5-tetrafluorobenzoyl)acrylonitrile

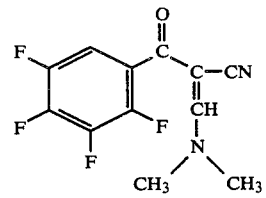

First 9.7 g of 3-dimethylaminoacrylonitrile are added dropwise, then 10.5 g of triethylamine are added to a solution of 21.25 g of 2,3,4,5-tetrafluorobenzoyl chloride in 75 ml of anhydrous dioxane, while cooling in ice and stirring at about 10°–15° C. The mixture is heated to boiling under reflux for 4 hours, the solvent is removed by distillation in vacuo, and the residue is taken up in methylene chloride/water. The phases are separated, and the aqueous solution is again extracted with methylene chloride. The combined organic phases are washed with water, dried with sodium sulphate, and the methylene chloride is removed in vacuo. After recrystallization of the crystalline residue from ethanol, 23.5 g of 3-dimethylamino-2-(2,3,4,5-tetrafluorobenzoyl)acrylonitrile of melting point 149°–151° C. are obtained.

It will be understood that the specification and examples are illustrative but not limitative of the present invention and that other embodiments within the spirit and scope of the invention will suggest themselves to those skilled in the art.

I claim:

1. A 3-amino-2-benzoylacrylic acid derivative of the formula

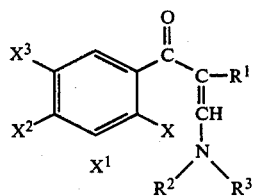

in which
$R^1$ represents the nitrile group or an ester group —COOR$^4$
$R^4$ denotes $C_1$–$C_6$-alkyl,
$R^2$ and $R^3$, which can be identical or different, represent a $C_1$–$C_6$-alkyl radical,
X, $X^2$ and $X^3$ represent halogen, and
$X^1$ denotes hydrogen, methyl, nitro or halogen.

2. A compound according to claim 1, wherein such compound is methyl 3-dimethylamino-2-(2,4-dichloro-5-fluorobenzoyl)acrylate.

3. A compound according to claim 1, wherein such compound is ethyl 3-dimethylamino-2-(2,4-dichloro-5-fluorobenzoyl)acrylate.

4. A compound according to claim 1, wherein such compound is 3-dimethylamino-2-(2,3,4,5-tetrafluorobenzoyl)acrylonitrile.

5. A compound according to claim 1, wherein such compound is 3-dimethylamino-2-(2,4-dichloro-5-fluorobenzoyl)-acrylonitrile.

6. A process for the preparation of a 3-cyclopropylamino-2-benzoylacrylic acid derivative of the formula

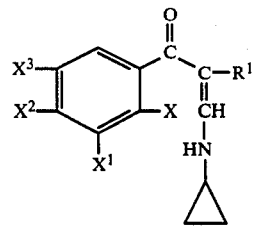

in which
$R^1$ represents the nitrile group, an ester group —COOR$^4$ or carboxamide group

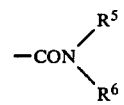

$R^4$ denoting $C_1$–$C_6$-alkyl, and
$R^5$ and $R^6$ representing hydrogen or $C_1$–$C_3$-alkyl or phenyl,
X represents halogen,
$X^1$ denotes hydrogen, methyl, nitro or halogen,
$X^2$ denotes halogen or methyl, and
$X^3$ denotes hydrogen or halogen,
comprising reacting a benzoyl halide of the formula

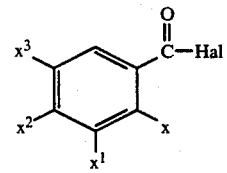

in which
Hal denotes halogen,
with a 3-aminoacrylic acid derivative of the formula

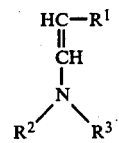

in which
$R^2$ and $R^3$, which can be identical or different, represent a $C_1$–$C_6$-alkyl radical,
thereby to produce the compound of the formula

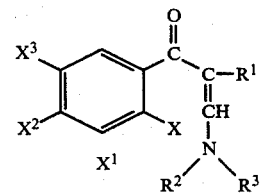

and reacting such compound with cyclopropylamine.

* * * * *